Figure 1:
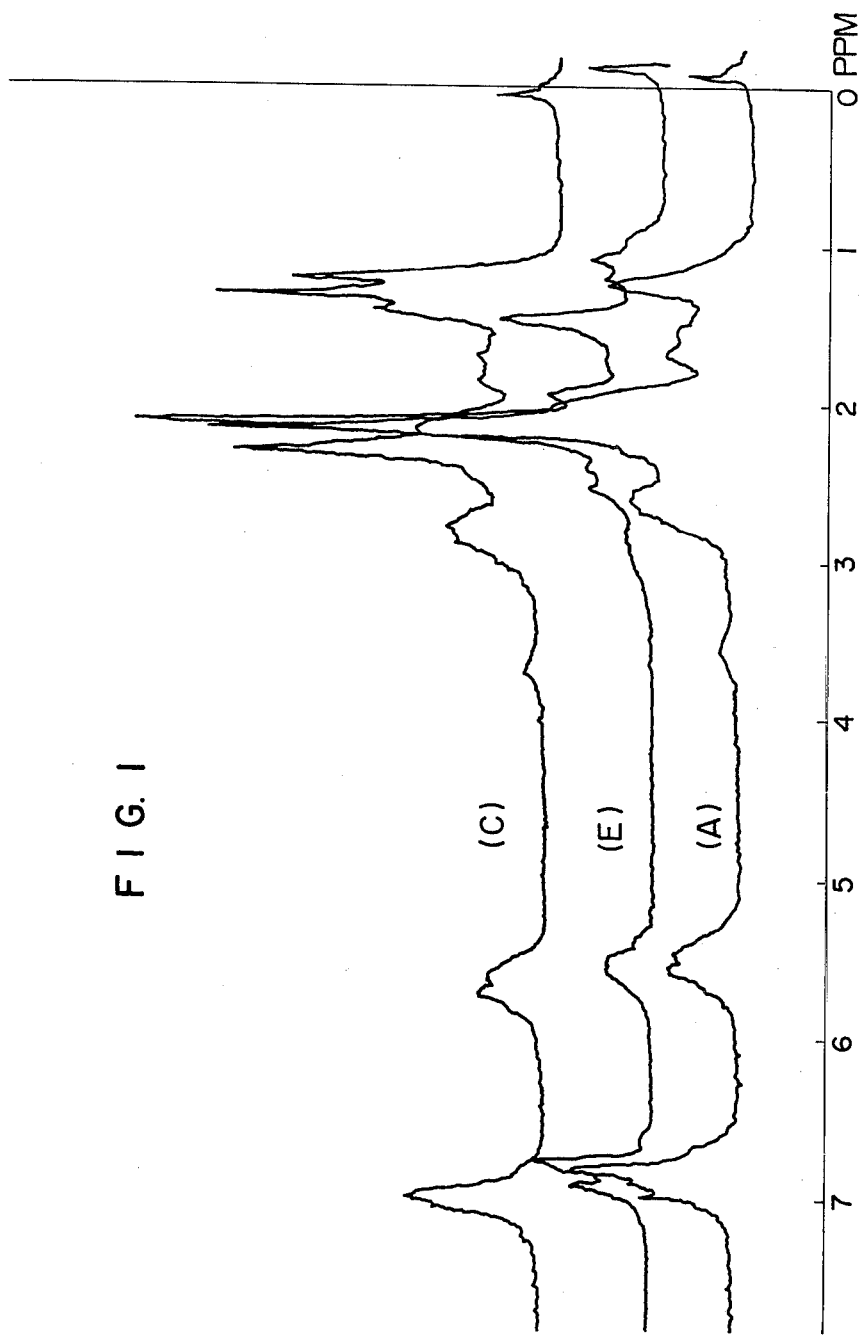

United States Patent [19]

Arakawa et al.

[11] 4,138,419

[45] Feb. 6, 1979

[54] CYCLOPENTADIENE DERIVATIVE

[75] Inventors: Masatoshi Arakawa; Ryotaro Ohno; Katuhiro Ishikawa; Noboru Yamahara; Hisashi Matsui, all of Yokkaichi, Japan

[73] Assignee: Japan Synthetic Rubber Co., Ltd., Tokyo, Japan

[21] Appl. No.: 792,225

[22] Filed: Apr. 29, 1977

[30] Foreign Application Priority Data

May 6, 1976 [JP] Japan ................... 51-50908

[51] Int. Cl.² ..................... C07C 63/36; C07C 63/44; C07C 69/76
[52] U.S. Cl. .......................... 260/429 R; 260/29.7 R; 260/31.2 R; 260/429.9; 260/434; 260/293.62; 260/501.1; 260/501.2; 260/501.17; 162/164 R; 162/179; 106/20; 106/287 R; 106/287.24; 106/287.25; 252/367; 560/102; 562/406; 562/492; 546/195; 546/203
[58] Field of Search ................... 560/102; 260/515 R, 260/429.9, 429 R, 434

[56] References Cited

U.S. PATENT DOCUMENTS

| 3,928,414 | 12/1975 | Shimizu .......................... 560/102 |
| 3,992,433 | 11/1976 | Ariyoshi et al. ................ 260/468 G |
| 4,048,147 | 9/1977 | Arakawa et al. ............... 260/67 VA |

Primary Examiner—Jane S. Myers
Attorney, Agent, or Firm—Oblon, Fisher, Spivak, McClelland & Maier

[57] ABSTRACT

A novel cyclopentadiene derivative of the general formula:

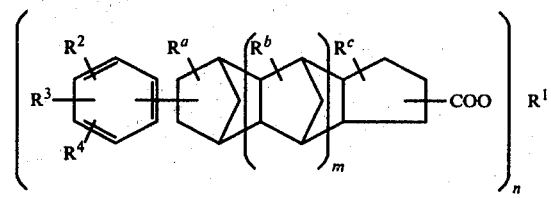

wherein $R^1$ is hydrogen, a mono- to tetra-hydric alcohol moiety having 1 to 12 carbon atoms, a metal of Groups Ia, IIa and IIb of the Periodic Table, an ammonium group or an organic amine residue; $R^2$, $R^3$, and $R^4$ are independently hydrogen or alkyl groups having 1 to 6 carbon atoms; $R^a$, $R^b$, and $R^c$ are independently hydrogen or alkyl groups having 1 to 3 carbon atoms; m is 0 or 1; and n is an integer of 1 to 4. This cyclopentadiene derivative is comparable or even superior to natural rosin in effectiveness as an emulsifier for use in the production of SBR and ABS resins or as a sizing agent in paper making.

14 Claims, 13 Drawing Figures

CYCLOPENTADIENE DERIVATIVE

This invention relates to a novel resinous compound containing in its molecule a cyclopentadiene skeleton, a benzene nucleus, and a carboxyl group and, more particularly, to a resin comparable in performance characteristics to natural rosin.

Natural rosin and its derivatives have been widely used in various fields because of its carboxyl group present in its molecule and other structural characteristics. For instance, alkali metal salts of natural rosin have an excellent anionic surface activity and are used as emulsifiers in manufacturing a styrenebutadiene rubber (SBR), an acrylonitrile-butadienestyrene resin (ABS resin), or the like, by emulsion polymerization. The SBR or ABS resin manufactured by use of such an emulsifier exhibit more desirable performance characteristics on account of a tackifying effect of the natural rosin.

Further, owing to appropriate softening point, sufficient solubility in many solvents, and excellent compatibility with various polymeric substances, polyol esters of natural rosin are widely used as a hot-melt adhesive and a tackifier for adhesive tape and exhibit properties superior to those of conventional synthetic resins.

Since natural rosin has an excellent sizing effect, an alkali metal salt of natural rosin is applied to a pulp as an internal or surface size in the papermaking industry to obtain Western-style paper which resists feathering when written with a water ink. Natural rosin is widely used also in other fields such as paints, printing inks, flooring tile materials, road materials, etc.

As described above, natural rosin and its derivatives have been utilized in many fields, exhibiting excellent properties in the respective fields, and have established a firm position not easily replaceable by conventional synthetic resins such as terpene and petroleum resins. Being a natural product, however, natural rosin is in limited supply and its price has been increased in recent years. Moreover, it has a further disadvantage of variation in quality depending on the area where it was produced and the method by which it was processed. Consequently, advent of a synthetic resin comparable in properties to natural rosin has been eagerly desired. Under the circumstances, the present inventors have conducted extensive studies on the manufacture of a synthetic resin which can be substituted for natural rosin, and, as a result, found that specific derivatives of cyclopentadiene have properties equivalent to those of natural rosin.

An object of this invention is to provide a novel resin having a cyclopentadiene skeleton, benzene nucleus, and carboxyl group.

Another object of this invention is to provide a novel resin comparable in performance characteristics to natural rosin.

A further object of this invention is to provide an emulsifier or a paper-sizing agent containing said novel resin as major component.

Other objects and advantages of this invention will become apparent from the following description.

According to this invention, there is provided a cyclopentadiene derivative of the general formula:

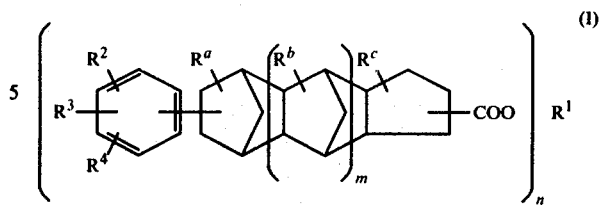

wherein $R^1$ is hydrogen, a mono- to tetra-hydric alcohol moiety having 1 to 12 carbon atoms, a metal of Groups Ia, IIa and IIb of the Periodic Table, an ammonium group or an organic amine residue; $R^2$, $R^3$, and $R^4$ are independently hydrogen or alkyl groups having 1 to 6 carbon atoms; $R^a$, $R^b$, and $R^c$ are independently hydrogen or alkyl groups having 1 to 3 carbon atoms; m is 0 or 1; and n is an integer of 1 to 4. Generally, n is 1 when $R^1$ is hydrogen or a metal of Group Ia of the Periodic Table, such as sodium or potassium; n is 2 when $R^1$ is a metal of Group IIa and IIb of the Periodic Table such as calcium, zinc, or magnesium; n is 1 when $R^1$ is an ammonium group or an organic amine residue; and n is 1 to 4 corresponding to the number of substituted hydroxyl groups of an alcohol when $R^1$ is an alcohol moiety.

The alcohol moiety $R^1$ in the formula (I) is derived from a mono- to tetra-hydric alcohol having 1 to 12, preferably 1 to 6 carbon atoms. Such alcohols include methanol, ethanol, propanol, butanol, pentanol, hexanol, octanol, decanol, dodecanol, ethylene glycol, propylene glycol, butylene glycol, diethylene glycol, triethylene glycol, trimethylolethane, trimethylolpropane, glycerol, pentaerythritol, cyclohexanol, and benzyl alcohol. Of the above alcohols, glycerol and pentaerythriol are particularly useful when the present compound is used in paints or adhesives.

Preferable examples of the Group Ia metals are sodium and potassium; and preferable examples of the Group IIa and IIb metals are calcium, zinc, and magnesium.

The organic amine residue is derived from an organic amine. Examples of preferable organic amines include alkylamines such as methylamine, ethylamine, propylamine, diethylamine, dimethylamine, trimethylamine, triethylamine, butylamine, dibutylamine, and tributylamine; polyamines such as ethylenediamine, diethylenetriamine, and triethylenetetramine; alkanolines such as triethanolamine, diethanolamine, monoethanolamine, triisopropanolamine, N,N-dimethylethanolamine, and N-methyl-N,N-diethanolamine; morpholine; and piperidine.

In the compound of this invention, the carbonyl group is attached to a carbon atom in the 1-, 2- or 3-position of the dicyclopentadiene or tricyclopentadiene as shown in the following formulas, and the benzene nucleus is attached to a carbon atom in the 5- or 6-position of the above dicyclopentadiene or in the 6- or 7-position of the above tricyclopentadiene:

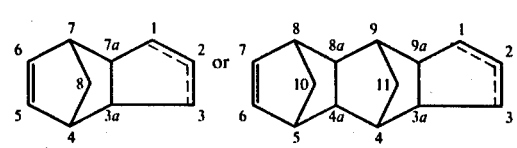

The compound of the formula (I) of this invention may be prepared by the following methods:

(1) Method for preparing an ester or a carboxylic acid by hydroesterification or hydrocarboxylation of a compound of the following formula (II):

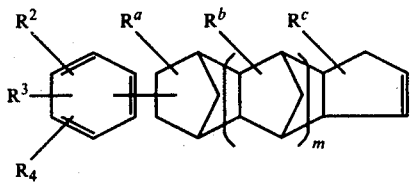

wherein $R^2$, $R^3$, and $R^4$ are independently hydrogen or alkyl groups having 1 to 6 carbon atoms; $R^a$, $R^b$, and $R^c$ are independently hydrogen or alkyl groups having 1 to 3 carbon atoms; and m is 0 or 1.

The hydroesterification and hydrocarboxylation can be effected by reacting the compound of the formula (II) with an alcohol and water, respectively, under a superatmospheric pressure of carbon monoxide using as catalyst a metal such as nickel, cobalt, or palladium, or a salt, an oxide, or a carbonyl compound of the metal.

The above alcohol is preferably methanol, ethanol, propanol, butanol, pentanol, or hexanol. Of these alcohols, particularly preferred are methanol, ethanol, and propanol.

The amount of the alcohol used is 1 to 30, preferably 1 to 10, moles per mole of the compound of the formula (II).

The reaction pressure is 10 to 300, preferably 40 to 150 atom., and the reaction temperature is 80° to 300°, preferably 100° to 200° C. The amount of the catalyst used is 0.3 to 30, preferably 1 to 10, mole % based on the compound of the formula (II).

As another procedure, the Koch reaction may be utilized by reacting the compound of the formula (II) with water under a superatmospheric pressure of carbon monoxide as in the above reaction using as catalyst concentrated sulfuric acid, concentrated phosphoric acid, hydrogen fluoride, boron trifluoride or the like. In this case, a reaction pressure of 1 to 150 atom. and a reaction temperature of 0° to 100° C. are desirable. The amount of the catalyst used is 1 to 50, preferably 5 to 20, moles per mole of the compound of the formula (II).

The same product may be produced by hydroformylating a compound of the formula (II) and then oxidizing the hydroformylation product, without directly hydrocarboxylating the compound of the formula (II). The hydroformylation reaction is carried out in a gaseous mixture of hydrogen and carbon monoxide at a high temperature under a high pressure using as catalyst a metal such as cobalt or rhodium, or a salt, an oxide, or a carbonyl compound of the metal. The oxidation reaction includes oxidation using platinum or palladium as catalyst, or oxidation with chromic acid, or permanganic acid, and oxidation with an alkali.

The starting material of the formula (II) used in the above method (1) can be prepared by Friedel-Crafts reaction between a compound of the following formula (III) and one of the cyclopentadienes of the following formula (IV) such as dicyclopentadiene, an alkylsubstituted dicyclopentadiene, tricyclopentadiene, or an alkyl-substituted tricyclopentadiene:

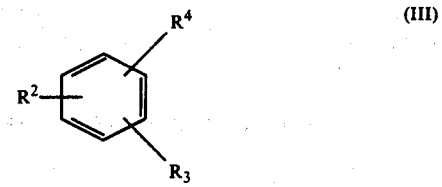

wherein $R^2$, $R^3$, and $R^4$ are independently hydrogen or alkyl groups having 1 to 6 carbon atoms, and

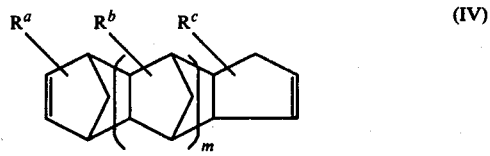

wherein $R^a$, $R^b$, and $R^c$ are independently hydrogen or alkyl groups having 1 to 3 carbon atoms and m is 0 or 1.

Examples of the compounds of the formula (III) include, for instance, benzene and mono-, di-, and trialkyl-substituted benzenes in which the alkyl group has 1 to 6 carbon atoms, such as toluene, ethylbenzene, cumene, cymene, xylene, 1,2,4-trimethylbenzene, butylbenzene, sec-butylbenzene, tert-butylbenzene, hexylbenzene, and di-tert-butylbenzene. Tetrahydronaphthalene, which is di-alkylbenzene in which the two alkyl groups join to each other to form a ring, may also be used. Of the compounds of the formula (III), particularly preferred are benzene, toluene, cumene, cymene, and xylenes.

The compounds of the formula (IV) are dimers and trimers of cyclopentadienes. Cyclopentadienes include cyclopentadiene (CPD) and alkylcyclopentadienes such as methylcyclopentadiene, ethylcyclopentadiene, propylcyclopentadiene and the like. Of these, CPD is preferred in view of the availability of the raw material and economy.

The dimer of one kind of cyclopentadiene and codimers of two kinds of cyclopentadienes include dicyclopentadiene (DCPD), codimers of CPD and an alkylcyclopentadiene, dimers of one kind of alkylcyclopentadiene, and codimers of two kinds of alkylcyclopentadienes. Of these, DCPD is most preferred in view of the availability of the raw material and economy. DCPD can easily be obtained by dimerization of CPD contained in the $C_5$-fraction resulting from naphtha cracking. During the dimerization of the $C_5$-fraction, a codimer of CPD and a straight chain conjugated diene such as isoprene is formed as a by-product. Said codimer contains a codimer having a norbornene ring, and even in this case, the codimer may be used for the purpose of this invention.

In the case of trimers of the formula (IV), circumstances are similar to those in the case of dimers. Among trimers, tricyclopentadiene is most preferred from the viewpoint of availability and economy.

As the catalysts in the above Friedel-Crafts reaction, there may be used sulfuric acid, phosphoric acid, hydrogen fluoride, boron trifluoride, boron trifluoride complexes, aluminum chloride, aluminum bromide, tin tetrachloride, zinc chloride, titanium trichloride, and the like. Although the compound of the formula (IV) has two double bonds active to the Friedel-Crafts reaction, the double bond in the norbornene ring is more reactive and, hence, the compound of the formula (II) is preferentially formed in a greater proportion. However, since the compound of the formula (II) still retains a reactive double bond in its five-membered ring, it is necessary to keep the reaction time from being unduly prolonged. The catalyst concentration may be as low as 0.5 to 10% by weight based on the compound of the formula (IV).

The compound of the formula (II) may also be prepared by Friedel-Crafts reaction between the compound of formula (III) and the compound of the following formula (V):

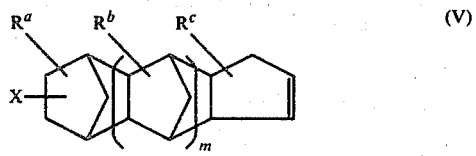

wherein $R^a$, $R^b$, and $R^c$ are hydrogen or alkyl groups having 1 to 3 carbon atoms; m is 0 or 1; and X is a hydroxyl group or a halogen atom. The catalyst for use in the above reaction may be any of the known Friedel-Crafts catalysts.

(2) Method for reacting a compound of the formula (III) and a compound of the formula (VI):

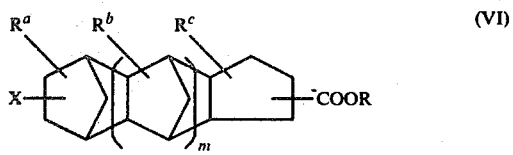

wherein m is 0 or 1; X is a hydroxyl group or a halogen atom; R is hydrogen or an alkyl group having 1 to 5 carbon atoms; and $R^a$, $R^b$, and $R^c$ are independently hydrogen or alkyl groups having 1 to 3 carbon atoms, by using a Friedel-Crafts catalyst.

The above Friedel-Crafts reaction can be carried out by using a known catalyst such as sulfuric acid, phosphoric acid, hydrogen fluoride, boron fluoride or a boron fluoride complex, aluminum chloride, aluminum bromide, tin tetrachloride, zinc chloride, or titanium trichloride. The starting material of the formula (VI) can be prepared by the hydrocarboxylation or hydroesterification of the compound of the formula (V). These reactions can be carried out in a manner similar to that described in the above method (1), though application of the Koch reaction is undesirable in this case.

The carboxylic acid may also be prepared by hydrolysis of the ester by use of an acid catalyst such as hydrochloric acid, sulfuric acid, acetic acid, aromatic sulfonic acid, and the like or an alkaline catalyst such as an alkali metal hydroxide, an alkaline earth metal hydroxide, or the like.

The ester may also be prepared by esterification of the carboxylic acid which may be effected with or without a catalyst such as sulfuric acid, hydrochloric acid, toluene-sulfonic acid, boron fluoride, or the like. Further, the ester may be prepared by transesterification (alcoholysis). In this case, there may be used, as catalyst, not only sulfuric acid, hydrochloric acid, toluenesulfonic acid, and boron fluoride, but also sodium alkoxide, ammonia, pyridine, and sodium hydroxide.

The carboxylic acid or ester of this invention can be easily transformed to a Group Ia metal salt, a Group IIa or IIb metal salt, amine salt, or ammonium salt by reacting it with a Group Ia metal hydroxide, a Group IIa or IIb metal hydroxide, an amine, or ammonia, respectively, at 0° to 300° C.

The present compound of the formula (I) has properties and performance characteristics similar to those of natural rosin or its derivative and can similarly be used in a field such as emulsifiers, paper sizing agents, adhesives, paints, printing inks, rubber molded articles, molded articles of plastics, road materials, etc. The examples thereof are as follows:

(I) The case of water-soluble salts (Group Ia metal salt, ammonium salt, amine salt) of the carboxylic acid:

These salts show excellent surface activity and are very useful as an emulsifier for emulsion polymerization, particularly in manufacturing synthetic rubbers and resins such as SBR and ABS by emulsion polymerization, and as a paper sizing agent, and also exhibit excellent properties when used as an emulsifier for emulsions of waxes, oils, and resins. Of these salts, an alkali metal salt is particularly useful as an emulsifier for use in emulsion polymerization of synthetic rubbers and as a paper sizing agent. Moreover, the alkali metal salts are stable because of the absence of double bond. When used as an emulsifier in emulsion polymerization of synthetic rubbers, the resinous carboxylic acid salt of this invention has an important advantage over natural rosin in that it can be used satisfactorily without any pretreatment such as disproportionation which is necessary to stabilize natural rosin. In paper making, a partially maleinized mixed rosin is used as the rosin sizing agent, whereas the resinous carboxylic acid salt of this invention can be used, without any modification, as a sizing agent to obtain a sizing effect as high as that of the partially maleinized rosin soap.

(II) The case of the esters with mono- or polyhydric alcohols:

These esters are well compatible with various rubbers and synthetic resins and are used as a tackifier or modifier for these materials. For instance, said esters are incorporated into natural rubber, SBR, styrene-butadiene block copolymer, styrene-isoprene block copolymer, or the like to prepare a pressure-sensitive adhesive; incorporated into an ethylene-vinyl acetate copolymer, ethylene-ethyl acrylate copolymer, wax, or the like to prepare a hot-melt type adhesive and a sealing agent; incorporated into polyethylene, polypropylene, ethylene-vinyl acetate copolymer, or the like, and then shaped into a film or sheet; or incorporated into a vinyl chloride-based resins to prepare a floor tile.

(III) The case of carboxylic acids:

The carboxylic acids are suitable not only for the uses described in the case (II), but also for use as modifier for polyester resins. The modified polyesters are used as a binder for paints and trafic signal materials.

(IV) The case of salts with Group IIa or IIb metals such as magnesium, calcium, zinc, and the like:

These salts are resins having a high softening point and are used as a binder for printing inks and flooring tiles containing vinyl chloride-based resins.

(V) The case of the carboxylic acids or esters:

The carboxylic acids or esters are formed into an aqueous emulsion by use of a nonionic or cationic surface active agent. The aqueous emulsion as prepared is used as a surface coating material either alone or in combination with a high polymer emulsion such as a rubber latex or an acrylic resin emulsion. Such a surface coating material is applicable to surfaces of various materials. Emulsions of the carboxylic acids can also be used as a paper sizing agent similarly to the rosin emulsion.

The compound of the formula (I) of this invention can be further improved in thermal stability and weather resistance by hydrogenation to saturate its aromatic ring. When used as a paper sizing agent, the alkali metal salts of the hydrogenated compound exhibit better effect than unhydrogenated ones. The hydrogenation can be effected by a known method. For instance, it is carried out in the presence of a catalyst under a hydrogen pressure of 1 to 300 kg/cm$^2$ (gauge) at a temperature of room temperature to 250° C. for a period of 1 to 10 hours. As the catalyst, there may be used metals such as nickel, cobalt, palladium, platinum, ruthenium, rhenium, rhodium and the like, and oxides thereof, which may be supported on diatomaceous earth, carbon, alumina, silica gel, or the like. The amount of the catalyst used is generally 0.05 to 20% by weight based on the compound of the formula (I). In the above hydrogenation, the compound of the formula (I) can be used either as such or as a solution in an organic solvent such as n-hexane, cyclohexane, tetrahydrofuran, or the like, or, in case of alkali metal salts, as an aqueous solution.

Figure 2:
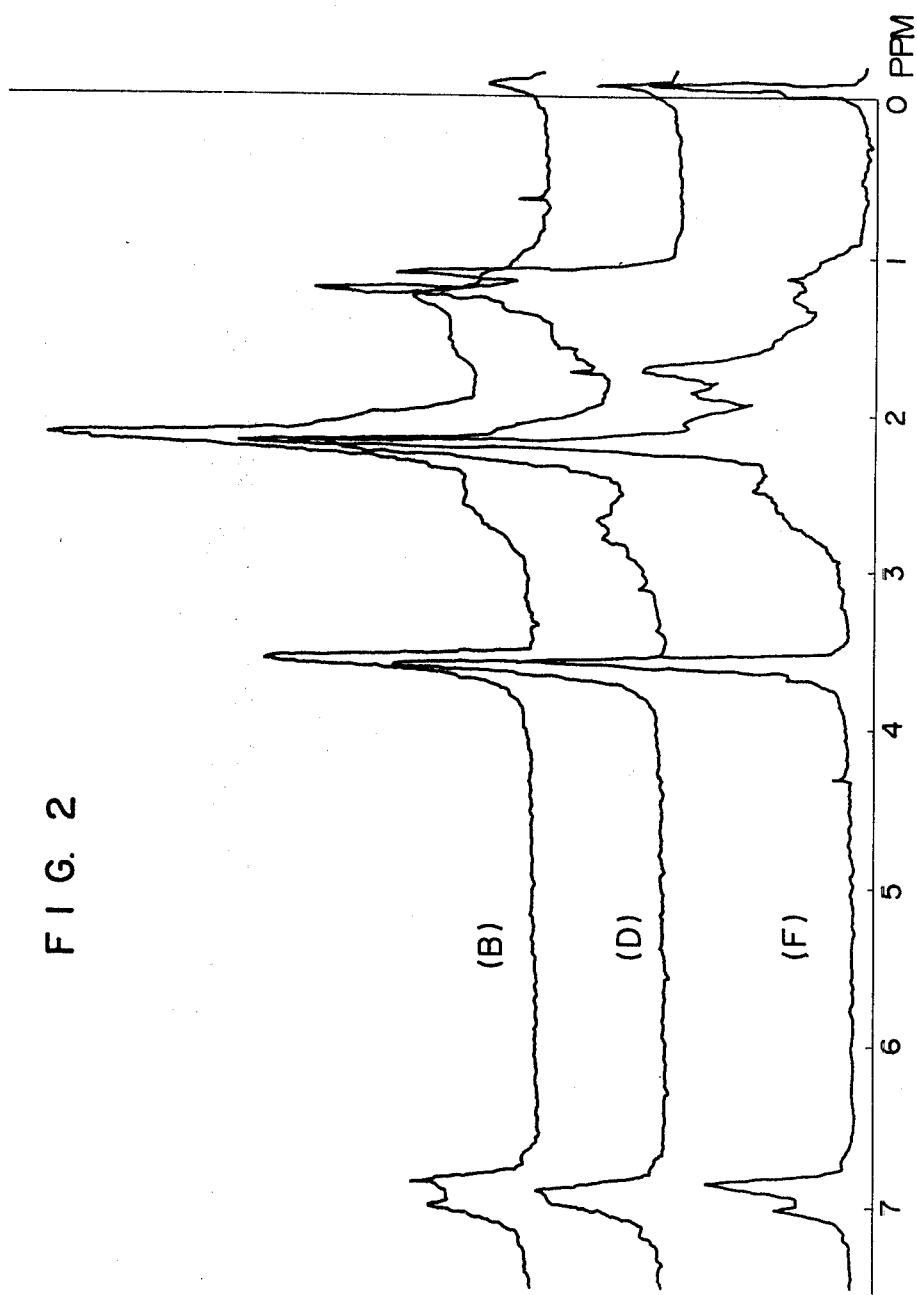
Figure 9:
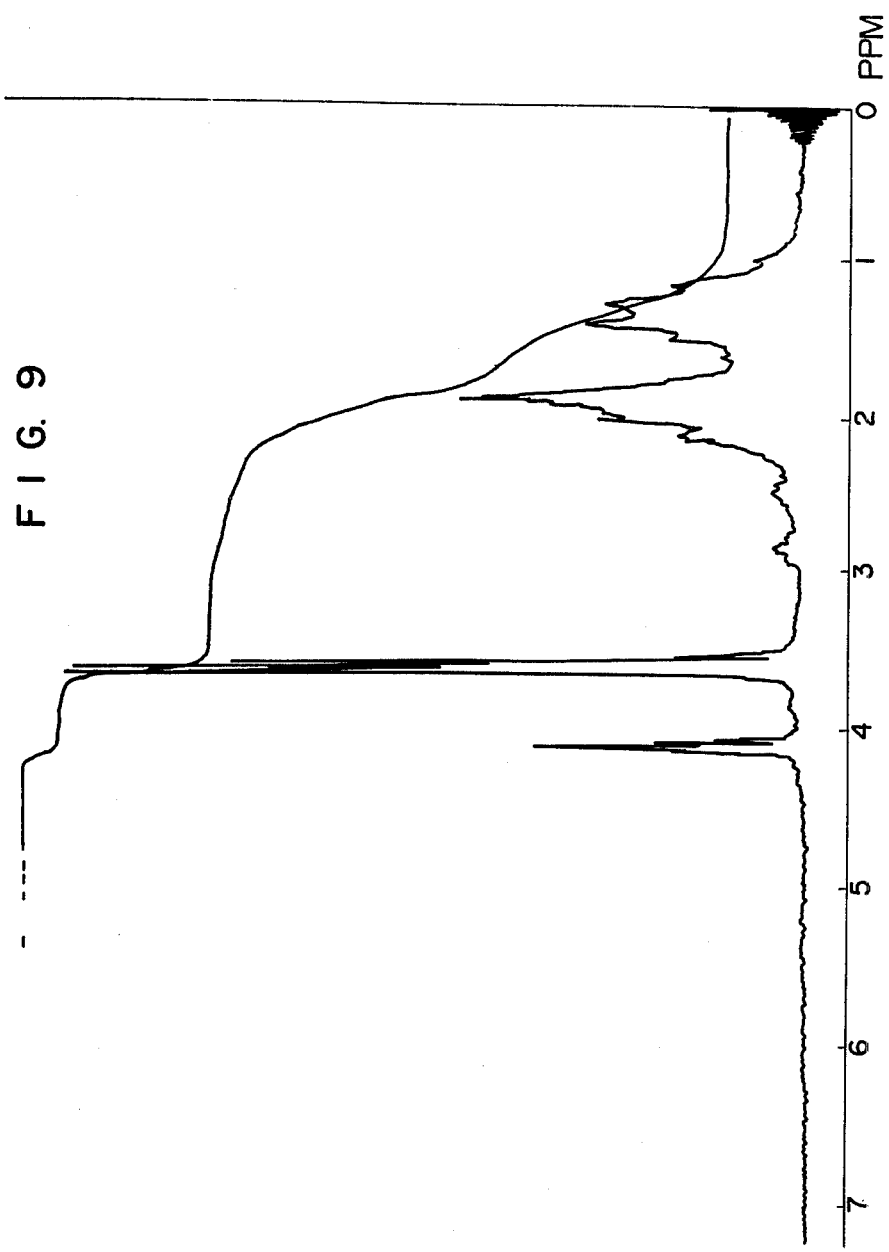

The accompanying drawings show NMR spectra and IR spectra of some of the compounds of this invention, wherein FIGS. 1, 2, and 9 show NMR spectra of compounds (A), (B), (C), (D), (E), (F), and (G) obtained in Examples 1, 2, 3, and 4 which appear hereinafter, and FIGS. 3 to 8 and 10 to 13 show IR spectra of compounds (A), (B), (B'), (C), (D), (D'), (E), (F), (F'), and (G) obtained in Examples 1 to 4.

The invention is further explained below in detail with reference to Examples which, however, are merely by way of illustration and not by way of limitation. In the Examples, NMR was measured on a 30% sample solution in carbon tetrachloride at 24° C.

EXAMPLE 1

(1) Friedel-Crafts reaction.

In a 5-liter, three-necked flask provided with a reflux condenser and a stirring device were placed 2,120 g of xylene and 20 g of BF$_3$-phenol complex, and the flask was then heated to 50° C. To the flask was added dropwise with stirring a mixture of 695 g of dicyclopentadiene having a purity of 95% and 530 g of xylene over a period of about one hour. After the dropwise addition, reaction was allowed to continue for a further 2 hours at said temperature. After the completion of the reaction, an aqueous solution of sodium carbonate was added to decompose the catalyst. The reaction mixture was washed with water and the oily layer was distilled in vacuo. The vacuum distillation was continued to remove the low-boiling substances including unreacted components until the temperature of the liquid had reached 150° C./3 mmHg. The distillation residue, which amounted to 960 g, was redistilled and 690 g of a fraction boiling at 156°–161° C./3 mmHg was obtained.

Figure 3:
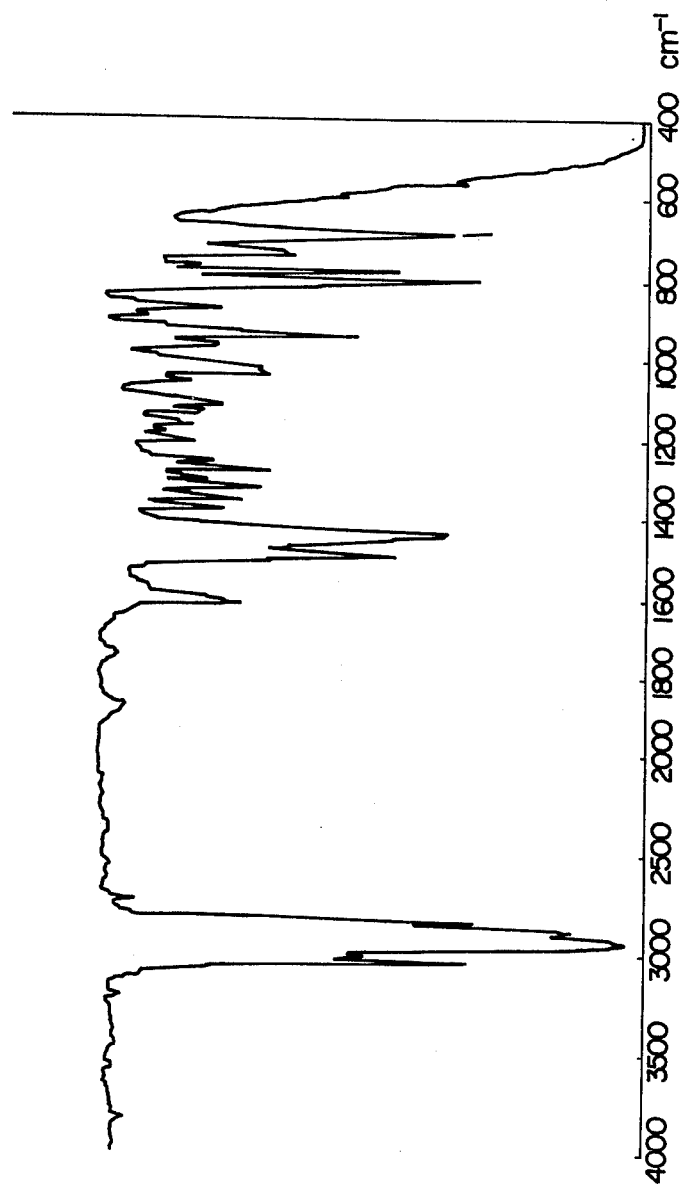
Figure 4:
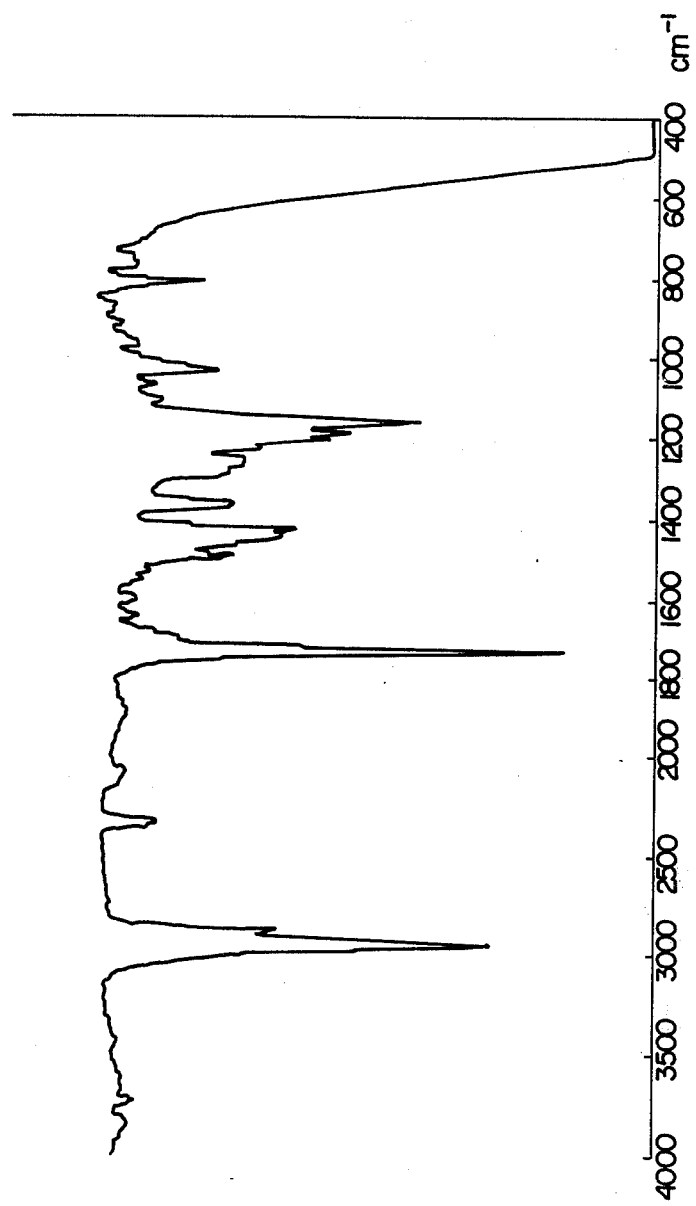
Figure 5:
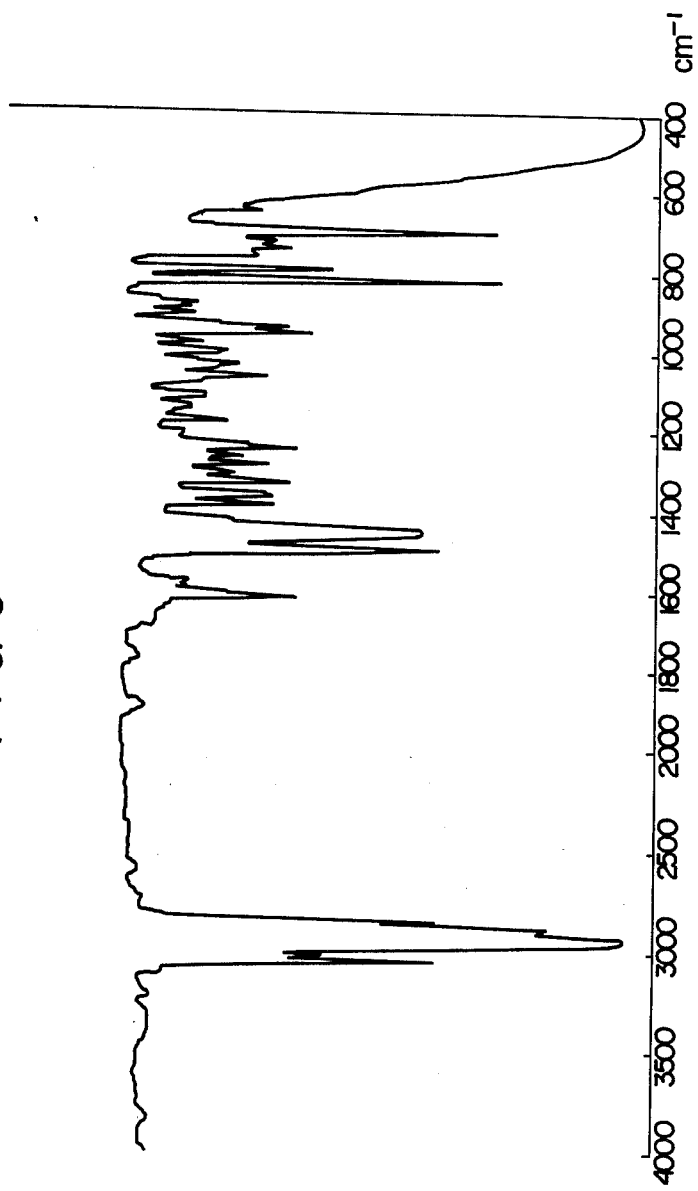

The liquid chromatogram of the above fraction showed a single peak, and the NMR spectrum thereof (carbon tetrachloride solution) showed that the protons of the double bond in the norbornene ring of the starting dicyclopentadiene had disappeared (5.88 ppm and 5.90 ppm); and the protons of the double bond in the cyclopentene ring remained at 5.4 ppm and the phenyl protons remained at 7.0 ppm [(A) in FIG. 1]. The IR spectrum of the fraction showed absorption at 700 and 1,620 cm$^{-1}$ due to the double bond in the cyclopentene ring and also showed absorption at 1,510 and 1,605 cm$^{-1}$ due to phenyl group (FIG. 3). The fraction had an iodine number of 104.

From the above analytical results, it was confirmed that the fraction had the following structural formula (A):

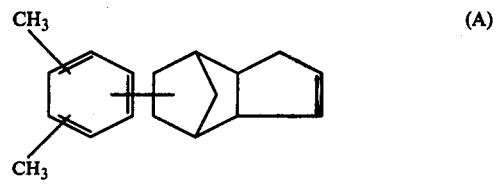

(2) Hydroesterification.

Into an autoclave were introduced 48 g of the fraction of the formula (A) obtained in above (1), 3 g of cobalt carbonate, 26 g of methanol, 14.4 g of pyridine, and 96 g of benzene. After the air in the autoclave had been replaced by hydrogen, carbon monoxide was introduced thereinto until a pressure of 90 kg/cm$^2$. The temperature in the autoclave was elevated to 190° C., at which temperature the reaction was allowed to proceed for 6.5 hours. After the completion of the reaction, the catalyst was decomposed with hydrochloric acid. The reaction mixture was washed with water and the oily layer was distilled to obtain 53 g of a fraction boiling at 180°–200° C./3 mmHg.

The above fraction showed a single peak in its liquid chromatogram and had a saponification number of 188. In the NMR spectrum of a carbon tetrachloride solution of the fraction, there were observed a signal due to phenyl protons at 6.9–7.1 ppm, a signal due to methyl ester protons at 3.6 ppm, and a signal due to protons of the methyl substituents on phenyl nucleus at 2.3 ppm, whereas the signal due to the protons of the double bond in the cyclopentene ring had disappeared [(B) in FIG. 2]. The IR spectrum of the fraction showed an absorption due to an ester group at 1,740 cm$^{-1}$ and an absorption due to a phenyl group at 1,510 and 1,605 cm$^{-1}$.

From the above analytical results it was confirmed that the fraction had the following structural formula (B):

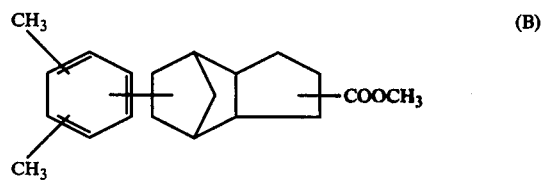

The fraction having the formula (B) was hydrolyzed by slowly adding it to a 48% aqueous potassium hydroxide solution containing KOH in an amount equivalent to the formula (B) ester and heating at 100° to 120° C. for 2 hours. The hydrolyzate solution was acidified with hydrochloric acid and the carboxylic acid was extracted with ethyl ether. The ether extract was distilled to obtain a mixture of position isomers of the following structural formula (B'):

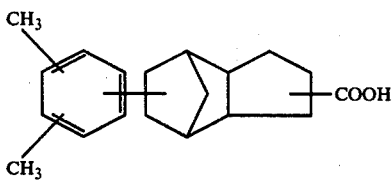

Figure 11:
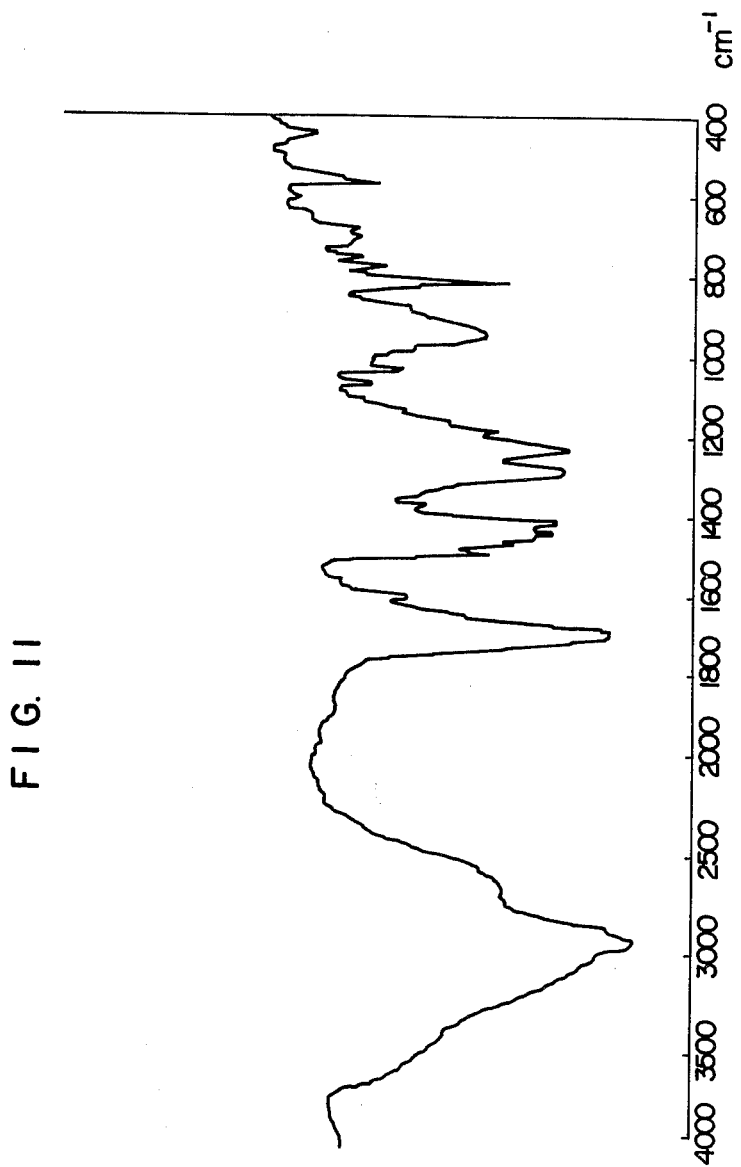

The formation of the position isomers was confirmed by means of NMR and IR spectra (FIG. 11).

EXAMPLE 2

(1) Friedel-Crafts reaction.

In the same manner as in Example 1, 670 g of cymene, 4 g of BF$_3$-phenol complex, and 139 g of dicyclopentadiene having a purity of 95% were allowed to react. By this method was obtained 96 g of a fraction having a boiling point of 165°–173° C./3 mmHg. From the NMR and IR spectra [(C) in FIG. 1, and FIG. 5] and the iodine number, it was confirmed that the fraction had the following structural formula (C):

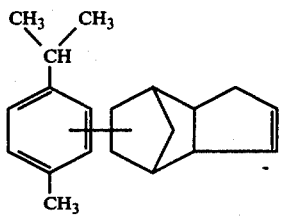

(2) Hydroesterification.

Into an autoclave were charged 53.3 g of the fraction having the formula (C), 4.1 g of cobalt octacarbonyl, 51 g of methanol, 9.5 g of pyridine and 53 g of benzene. After the air in the autoclave had been replaced by hydrogen, carbon monoxide was introduced thereinto until a pressure of 90 kg/cm$^2$. The temperature in the autoclave was elevated to 160° C., at which temperature the reaction was allowed to proceed for 5.5 hours. After the completion of the reaction, the reaction mixture was treated to decompose the catalyst, then washed with water and distilled to obtain 56 g of a fraction boiling at 190°–205° C./2 mmHg.

Figure 6:
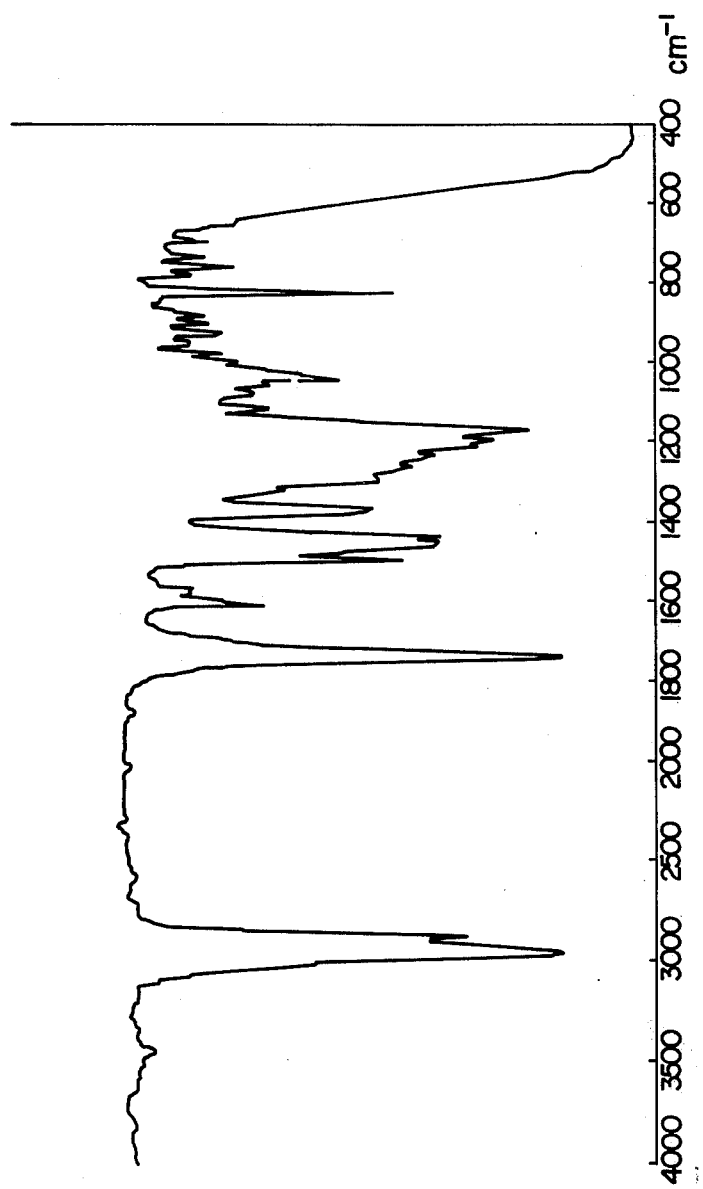

From the iodine number, liquid chromatogram, NMR spectrum, and IR spectrum, the above fraction was confirmed to be a mixture of position isomers having the following formula (D) [(D) in FIG. 2, and FIG. 6]:

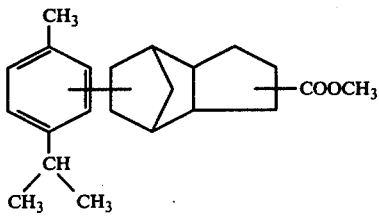

The fraction having the formula (D) was hydrolyzed by gradually adding it dropwise to a 48% aqueous potassium hydroxide solution containing KOH in an amount equivalent to the formula (D) ester and heating the mixture at 100° to 120° C. for 2 hours. The hydrolyzate solution was acidified with hydrochloric acid and the carboxylic acid was extracted with ethyl ether. The ether extract was distilled to obtain a mixture of position isomers of the formula (D'):

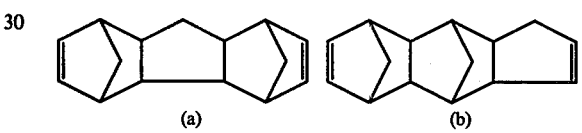

Figure 12:
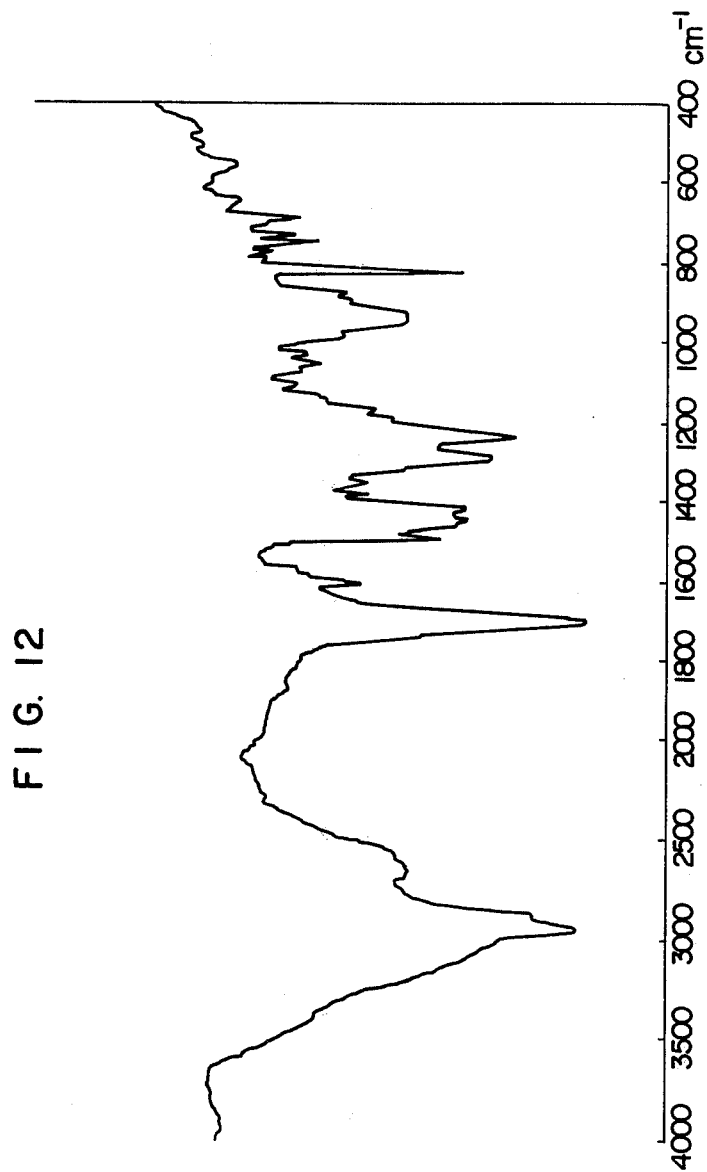

The formation of the position isomers was confirmed by means of NMR and IR spectra [FIG. 12].

EXAMPLE 3

(1) Friedel-Crafts reaction.

Into a 2-liter autoclave provided with an electromagnetic induction stirrer was charged 1 kg of dicyclopentadiene having a purity of 95%. The reaction was allowed to proceed at 190° C. for 3 hours. After the removal of 448 g of the unreacted substance, there were obtained 362 g of a fraction of cyclopentadiene trimer having a boiling range of 100° C./10 mmHg to 125° C./5 mmHg. From the results of gas chromatogram the fraction was found to be a mixture of the following isomers (a) and (b), each content being 12.9% of (a) and 87.1% of (b).

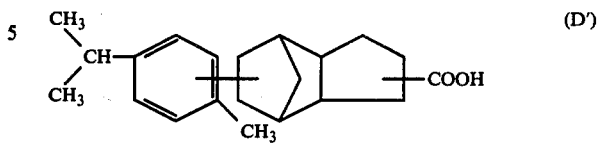

In a 3-liter, three-necked flask provided with a reflux condenser and a stirring device were charged 848 g of xylene and 10 g of BF$_3$-phenol complex, and the mixture was heated to 50° C. To the flask, while being maintained at this temperature, was added dropwise a mixture of 198 g of the cyclopentadiene trimer mixture obtained above and 212 g of xylene over a period of one hour. After the addition, reaction was allowed to continue for a further about 2 hours. After the completion of the reaction, an aqueous solution of sodium carbonate was added to decompose the catalyst. The reaction mixture was washed with water and the oily layer was distilled under reduced pressure. On removal of the unreacted xylene and others, 152 g of a fraction boiling at 182°–193° C./2 mmHg was obtained.

Figure 7:
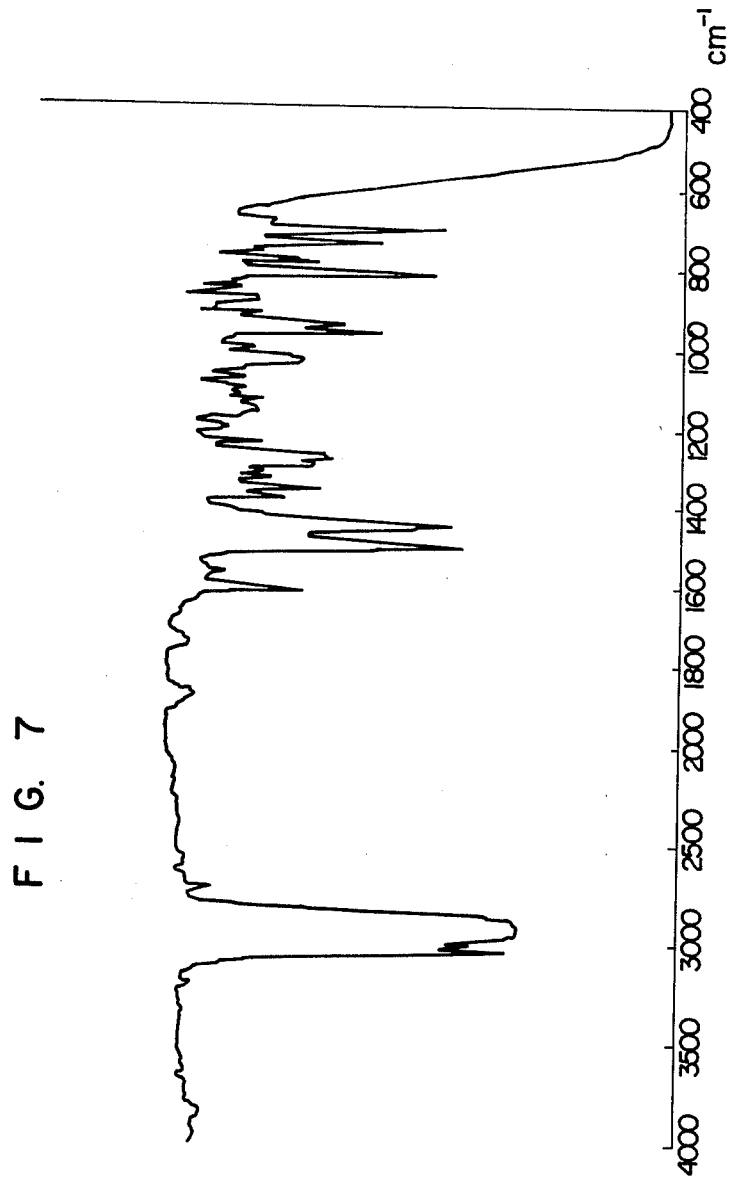
Figure 8:
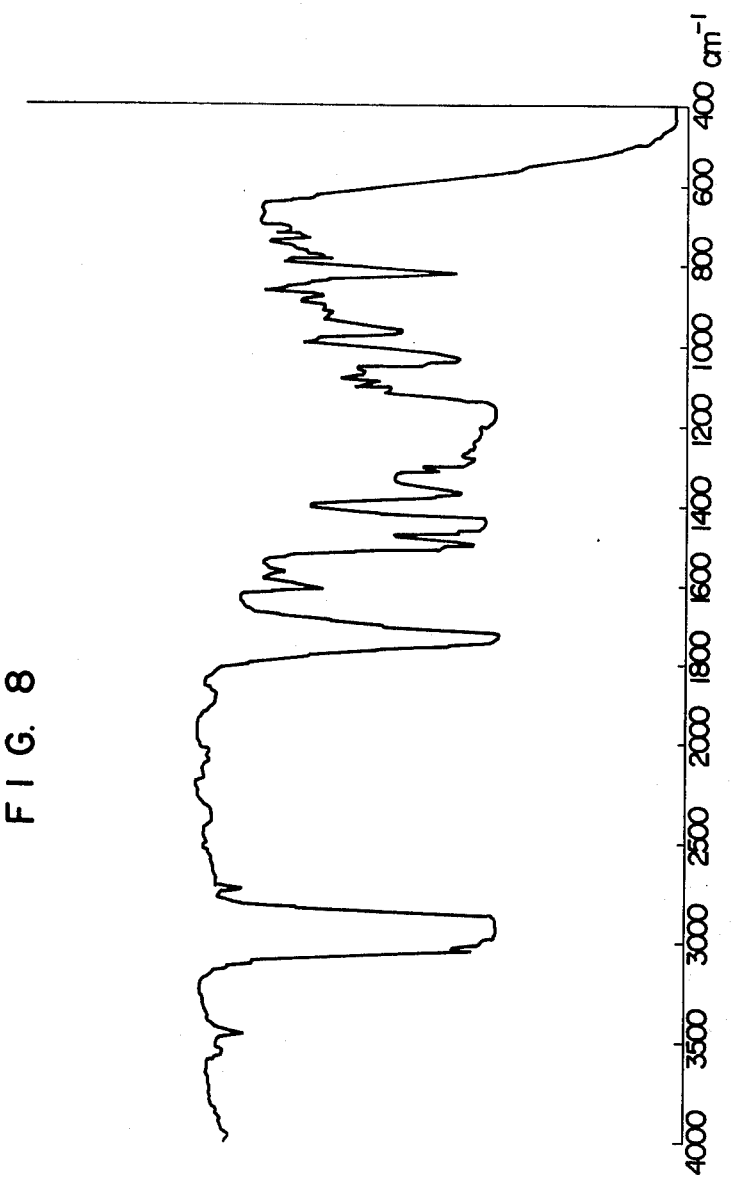

The above fraction was a colorless viscous liquid and its liquid chromatogram showed a single peak. In its NMR spectrum (carbon tetrachloride solution), signals (5.88 ppm, 5.90 ppm) due to protons of the double bond in the norbornene ring of the cyclopentadiene trimer used as the starting material had disappeared; while a signal at 5.4 ppm due to protons of the double bond in cyclopentene ring and a signal at 7.0 ppm due to protons of the phenyl group remained [(E) in FIG. 1]. IR spectrum showed absorption at 700 and 1,620 cm$^{-1}$ due to the double bond in the cyclopentene ring and at 1,510 and 1,605 cm$^{-1}$ due to phenyl group (FIG. 7). The fraction had an iodine number of 82.

It was confirmed from the above analytical results that the fraction had the following structural formula (E).

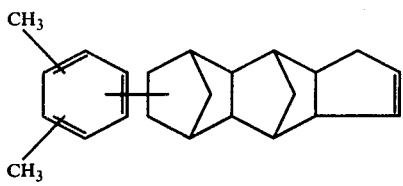

(E)

(2) Hydroesterification.

In the same manner as in Example 2, 66 g of a fraction boiling at 230°–245° C./2 mmHg were obtained from 61 g of the fraction of the formula (E) obtained in above (1), 4.1 g of cobalt octacarbonyl, 51 g of methanol, 9.5 g of pyridine, and 61 g of benzene. This fraction was confirmed to be a mixture of position isomers of the following formula (F) from its saponification number, liquid chromatogram, NMR spectrum, and IR spectrum [(F) in FIG. 2, and FIG. 8].

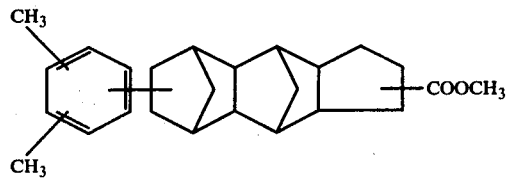

(F)

The fraction of the formula (F) was hydrolyzed by gradually adding it dropwise to a 48% aqueous potassium hydroxide solution containing KOH in an amount equivalent to the formula (F) ester and heating the mixture at 100° to 120° C. for 2 hours. The hydrolyzate solution was acidified with hydrochloric acid and the resulting carboxylic acid was extracted with ethyl ether. The ether extract was distilled to obtain a mixture of position isomers of the following formula (F').

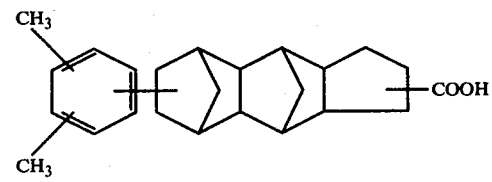

(F')

Figure 13:
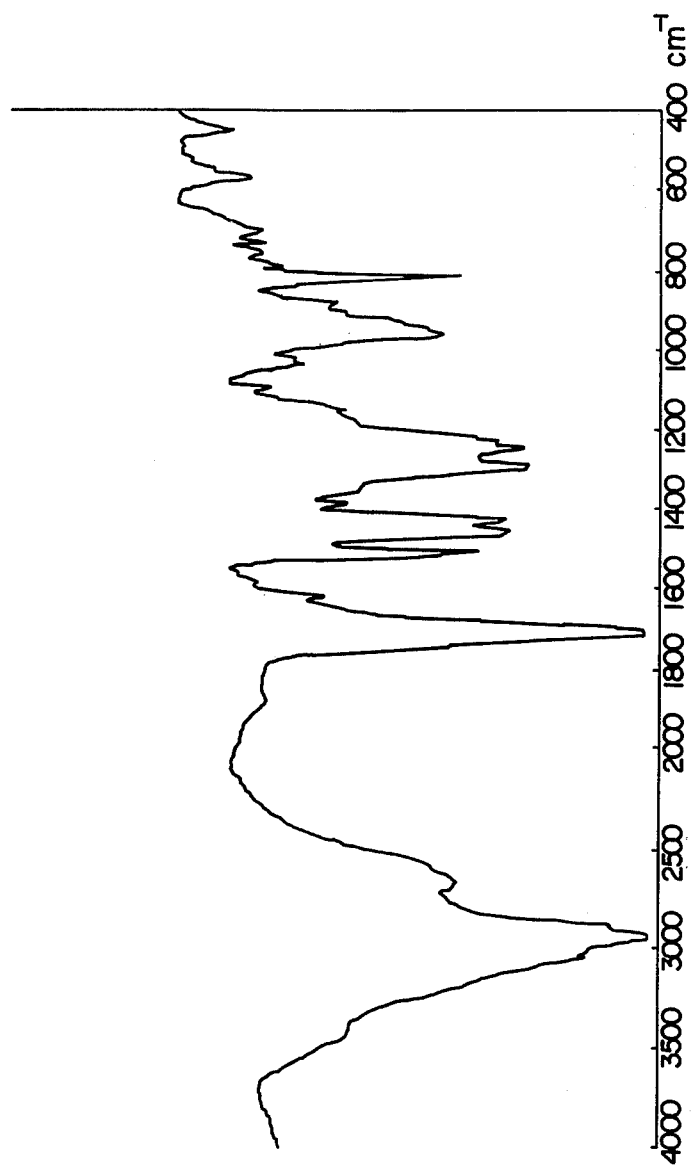

The formation of the position isomers was confirmed by means of NMR and IR spectra (FIG. 13).

EXAMPLE 4

(1) Friedel-Crafts reaction.

Into a 2-liter, three-necked flask were charged 396 g of dicyclopentadiene having a purity of 95% and 1,200 g of 25% sulfuric acid. The reaction was allowed to proceed at 80° C. for 5 hours. After the completion of the reaction, the reaction mixture was diluted with 300 ml of ethyl ether to separate an oily layer. The oily layer was washed first with water, then with an aqueous solution of sodium carbonate, and finally with water. The oily layer was dried overnight over anhydrous magnesium sulfate, and thereafter distilled under reduced pressure to obtain 272 g of hydroxydihydrodicyclopentadiene boiling at 100°–104° C./7 mmHg.

In the NMR spectrum of this substance (carbon tetrachloride solution), signals at 5.88 and 5.90 ppm due to protons attached to carbon atoms of the double bond in the norbornene ring of the starting dicyclopentadiene disappeared, while a signal at 3.7 ppm due to the proton of hydroxyl group (—OH) appeared. Said NMR spectrum, on the other hand, had signals at 5.4 ppm and 5.6 ppm due to protons attached to carbon atoms of the double bond in the five-membered ring The ratio between the total integrated intensity of these signals and that of the signal of —OH proton was 2:1. The IR spectrum showed absorption at 700 and 1,620 $cm^{-1}$ due to the double bond in the cyclopentene ring and a strong absorption at about 3,300 $cm^{-1}$ due to the hydroxyl group.

From the above facts, it was confirmed that the compound obtained had the following structural formula:

In a 300-ml, three-necked flask provided with a reflux condenser, a stirring device, and a dropping funnel were placed 60 g of xylene and 65 g of tin tetrachloride. To the flask maintained at 20° to 25° C. was added dropwise 30 g of the above hydroxydihydrodicyclopentadiene over a period of one hour. After the dropwise addition, stirring was continued for a further 0.5 hour. After the completion of the reaction, the catalyst was decomposed with an aqueous solution of sodium carbonate and the reaction mixture was then washed with water. The oily substance was distilled under reduced pressure. On removing the unreacted compounds and others by distillation, 18 g of a fraction boiling at 156°–161° C./3 mmHg was obtained. It showed a single peak in its liquid chromatogram. From NMR and IR spectra, this fraction was found to be identical with that of the formula (A) obtained in Example 1.

(2) Hydroesterification.

Into an autoclave were charged 150 g of the hydroxydihydrodicyclopentadiene obtained in above (1), 96 g of methanol, 24 g of pyridine, and 17.1 g of cobalt octacarbonyl [$Co_2(CO)_8$]. After carbon monoxide had been introduced thereinto until a pressure of 80 kg/cm$^2$ at room temperature, the contents were heated to 145° C. to allow the reaction to proceed at this temperature for 3.5 hours. After the completion of the reaction, the contents of the autoclave were withdrawn, diluted with 200 ml of ethyl ester, and washed with hydrochloric acid and water. After the removal of ethyl ether and others by distillation at ordinary pressure, the residue was subjected to distillation under reduced pressure to obtain 115 g of a colorless liquid boiling at 135°–138° C./1 mmHg.

Figure 10:
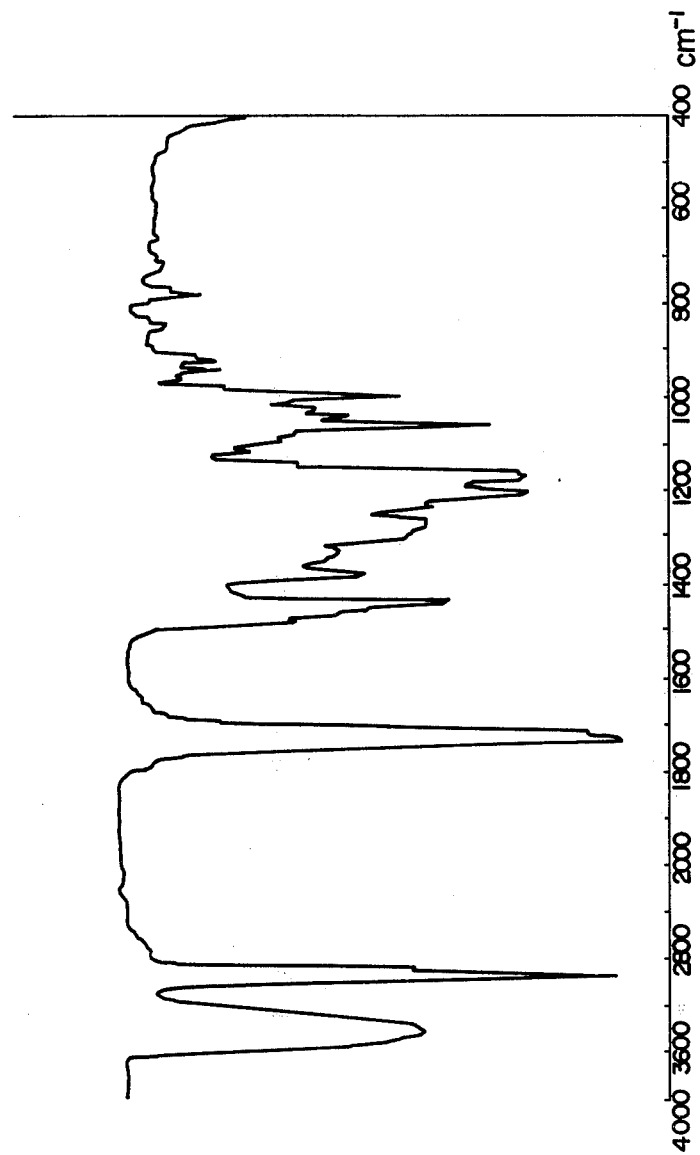

On examination of the NMR spectrum of the above colorless liquid, it was found that the signals at 5.4 ppm and 5.6 ppm belonging to the starting hydroxydihydrodicyclopentadiene disappeared and a signal due to protons of —COOCH₃ appeared instead at 3.6 ppm. Further, a signal due to the proton of —OH was present at 4.1 ppm (FIG. 9). The IR spectrum of said liquid showed absorption at 3,300 cm⁻¹ due to an alcohol and absorption at 1,740 cm⁻¹ due to an ester (FIG. 10). The liquid had a saponification number of 259 and an iodine number of 0. The elementary analysis values of the product were C 68.60%, H 8.57%, and O 22.86%, which were in good agreement with the theoretical values (68.55%, 8.63%, and 22.82%, respectively) of the compound of the formula (G) given below.

From the above analytical results, it was confirmed that the said fraction had the following formula (G):

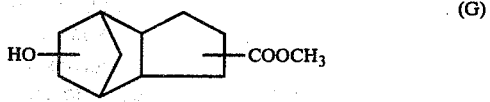
(G)

(3) Friedel-Crafts reaction.

In a 300-ml, three-necked flask provided with a reflux condenser, a stirring device, and a dropping funnel were placed 64 g of xylene and 15 g of anhydrous aluminum chloride. To the flask maintained at 50° C. was added dropwise 21 g of the above fraction of the formula (G) over a period of 5 hours. After the dropwise addition, the reaction was allowed to proceed for a further 3 hours. After the completion of the reaction, the catalyst was decomposed with an aqueous solution of sodium carbonate. The reaction mixture was then washed with water and the oily layer was distilled under reduced pressure. On removal of the unreacted compounds and others, 25 g of a fraction boiling at 180°–220° C./3 mmHg was obtained.

The above fraction showed two peaks in its liquid chromatogram. From the saponification number, acid number, IR spectrum, and NMR spectrum, it was confirmed that the above fraction was a mixture of the formula (B) fraction obtained in Example 1 and a carboxylic acid position isomer mixture formed by hydrolysis of said fraction.

EXAMPLE 5

(1) Friedel-Crafts reaction.

In a 3-liter, three-necked flask provided with a reflux condenser and a stirring device were placed 792 g of dicyclopentadiene having a purity of 95% and 1,200 g of 35% hydrochloric acid. The mixture was allowed to react at 80° C. for 5 hours. After having been cooled to room temperature, the reaction mixture was diluted with 500 ml of ethyl ether. The resulting solution was washed with water, then with an aqueous solution of sodium carbonate, and finally with water. The solution was dried overnight over anhydrous magnesium sulfate, and then freed from the ether by distillation under ordinary pressure. The residue was distilled under reduced pressure to obtain 708 g of a chlorodihydrodicyclopentadiene fraction boiling at 102°–104° C./10–12 mmHg.

The NMR spectrum of this fraction (carbon tetrachloride solution) showed no signal at 5.88 ppm and 5.90 ppm due to protons of the double bond in the norbornene ring of the starting dicyclopentadiene, but signals at 5.4 ppm and 5.6 ppm due to protons of the double bond in the cyclopentene ring. The IR spectrum showed absorption at 700 and 1,620 cm⁻¹ due to the double bond in the cyclopentene ring and at 650 cm⁻¹ due to the C-Cl bonding.

From the above results, it was confirmed that the fraction had the following formula:

In a 300-ml, three-necked flask provided with a reflux condenser, a stirring device, and a dropping funnel were placed 63 g of xylene and 22 g of zinc chloride. To the flask was added dropwise 27 g of the above chlorodihydrodicyclopentadiene over a period of one hour at 65° C. with stirring. After the dropwise addition, stirring was continued for a further 5 hours. After the completion of the reaction, the catalyst was decomposed with an aqueous solution of sodium carbonate and the reaction mixture was washed with water. The oily layer was distilled under reduced pressure to remove the unreacted compound and others. There was obtained 12 g of a fraction boiling at 156°–161° C./3 mmHg.

The above fraction showed a single peak in its liquid chromatogram. It was confirmed from NMR and IR spectra that the fraction was identical with the fraction of the formula (A) obtained in Example 1.

(2) Hydroesterification.

Into an autoclave were charged 105 g of the chlorodihydrodicyclopentadiene fraction obtained in above (1), 120 g of ethanol, and 0.60 g of PdCl₂-[P(C₆H₅)₃]₂. Carbon monoxide was introduced into the autoclave at room temperature until a pressure of 80 kg/cm². The temperature of the contents was elevated to 80° C. and the reaction was allowed to proceed for 4 hours. After the completion of the reaction, the contents of the autoclave was withdrawn, diluted with 200 ml of ethyl ether, washed with dilute hydrochloric acid and finally with water. After the ethyl ether and others had been removed by distillation under ordinary pressure, the resulting oily substance was distilled under reduced pressure to obtain 16 g of a colorless liquid boiling at 125°–130° C./1 mmHg.

The IR spectrum of the above liquid showed absorption at 1,740 cm⁻¹ due to an ester and at 650 cm⁻¹ due to C-Cl. The saponification number thereof was 231 and the iodine number was 0. The elementary analysis values were C 64.3%, H 7.8%, O 13.1%, and Cl 14.6%. It was confirmed from the above results that the liquid was a mixture of position isomers of the following structural formula (H):

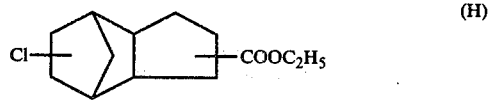
(H)

(3) Friedel-Crafts reaction.

In a 200-ml, three-necked flask provided with a reflux condenser, a stirring device, and a dropping funnel were placed 32 g of xylene and 28 g of anhydrous aluminum chloride. To the flask maintained at 50° C. was added dropwise 12 g of the position isomer mixture of the formula (H) over a period of 5 hours. After the dropwise addition, the reaction was allowed to proceed for a further 3 hours. After the completion of the reaction, the catalyst was decomposed with an aqueous solution of sodium carbonate and the reaction mixture was washed with water. The oily layer was distilled under reduced pressure to remove the unreacted compounds and others to obtain 14 g of a fraction boiling at 180°-220° C./3 mmHg.

The above fraction showed two peaks in its liquid chromatogram. From the saponification number, acid number, IR spectrum, and NMR spectrum, it was confirmed that the fraction was a mixture of an ethyl ester having the same structure as that of the fraction of the formula (B) obtained in Example 1, except that the methyl group of the ester group in formula (B) was replaced by ethyl group, and a corresponding carboxylic acid.

EXAMPLE 6

Emulsion polymerization test.

Each of the fractions of the formulas (B), (D), and (F) obtained in Examples 1, 2, and 3 was saponified with an aqueous solution of an equimolar quantity of potassium hydroxide at 78° C. for 2 hours. After removal of the liberated methanol, each reaction mixture was diluted with water to prepare a 25% aqueous solution. There were thus obtained aqueous solutions containing potassium salts, I, J, and K, of the carboxylic acids corresponding to the compounds (B), (D), and (F), respectively. These aqueous solutions were used as emulsifiers in sulfoxylate recipes for the manufacture of SBR of the cold-rubber type by emulsion polymerization and the percentage conversion was measured in each case.

The polymerization was carried out under a nitrogen atmosphere at 5° C. for 6 hours, using the recipe shown in Table 1.

Table 1

| Starting material and auxiliary material | | Amount (parts by weight) |
|---|---|---|
| Monomer | Butadiene | 70 |
| | Styrene | 30 |
| Dispersion medium | Deionized water (deairated) | 200 |
| Emulsifier | Aqueous solutions of I, J, and K (as solids) | 4.0 |
| | Naphthalene-formaldehyde resin sulfonic acid sodium salt | 0.15 |
| Modifier | tert-Dodecyl mercaptan | 0.245 |
| Initiator Oxidizing agent | p-Menthane hydroperoxide | 0.10 |
| Reducing agent | Ferrous sulfate (heptahydrate) | 0.05 |
| Secondary reducing agent | Sodium formaldehyde sulfoxylate | 0.15 |
| Chelating agent | Tetrasodium ethylenediamine-tetraacetate (EDTA-4Na) | 0.07 |
| Electrolyte | Sodium phosphate (dodecahydrate) | 0.80 |

Percentage conversion to SBR thus obtained were as shown in Table 2. In Table 2 is also shown the result obtained by use of a commercially available disproportionated rosin emulsifier, otherwise the polymerization procedure having been the same as mentioned above.

The stability of each latex was comparable to or better than that of the latex manufactured by use of a commercially available disproportionated rosin emulsifier.

Table 2

| Emulsifier | Conversion (%) |
|---|---|
| I | 72.1 |
| J | 69.5 |
| K | 64.8 |
| Commercially available disproportioned rosin emulsifier | 64.5 |

EXAMPLE 7

Sizing test.

A pulp of the L-BKP grade having a beating degree of 30° SR was dispersed in water to form a slurry of 1% consistency. To the slurry was added a prescribed amount of each of the same potassium salts, I, J, and K, as used in Example 6. Thereafter, an aqueous solution of hydrated aluminum sulfate was added to each slurry until pH becomes 4.5 After the pulp had been thoroughly dispersed, the slurry was made into a web on a TAPPI standard sheet machine. The wet web was pressed until a water content of 60 ± 1% was reached. The web was then dried at 80° C. for 5 minutes and made into a sheet form, 64.2 g/m$^2$ in basis weight. After having been conditioned for 24 hours in a conditioning cabinet at 20° C. and 65% R.H., the sheet specimen was tested for sizing effect according to the Stöckigt method. A commercially available fortified rosin size was used as control.

Table 3

| Amount of size added | 0.2% by weight | Unit: second 0.5% by weight |
|---|---|---|
| I | 24.8 | 32.5 |
| J | 26.0 | 34.2 |
| K | 23.0 | 31.5 |
| Fortified rosin size | 25.8 | 32.7 |

EXAMPLE 8

Printing ink test.

One hundred grams of the position isomer mixture of the formula (F') prepared in Example 3 was melted by heating at 220° C. To the molten mixture maintained at 220° C. was added 0.5 g of calcium acetate. To the mixture, after having been heated to 240° C., was added 7 g of calcium hydroxide over a period of 20 minutes. The resulting mixture was heated to 260° C. to allow the reaction to proceed at this temperature for 30 minutes and then discharged to obtain a calcium salt of this invention having a softening point of 164° C. and an acid number of 60. The formation of this salt was confirmed by the chelate titration method.

The above calcium salt was dissolved in toluene to prepare a 50% varnish. A mixture of 88 parts by weight of said varnish and 12 parts by weight of a pigment (Carmine 6B) was milled on a sand mill to obtain a printing ink. When applied to a gravure paper, this ink showed an excellent drying property. Gloss and printability were also favorable.

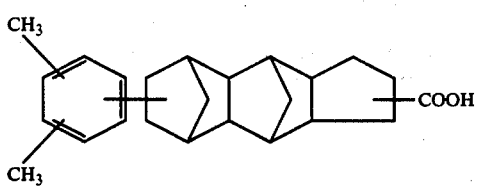

(F')

EXAMPLE 9

Adhesive test.

A mixture of 100 g of the carboxylic acid of the formula (B') obtained in Example 1 and 11.9 g of glycerol was heated at 170° C. to melt the mixture, and further heated, while removing the liberated water, to 250° C. in two hours. The reaction mixture was maintained at this temperature for an additional 5 hours to obtain a glycerol ester having a softening point of 75° C. The formation of this ester was confirmed by means of NMR and IR spectra.

A hot-melt adhesive was prepared by melting together and mixing uniformly 1 part by weight of the above glycerol ester, 1 part by weight of an ethylenevinyl acetate copolymer (vinyl acetate content: 28% by weight) having a melt index of 150 g/10 minutes, and 1 part by weight of a paraffin wax having a melting point of 157° F. This adhesive showed a stable melt viscosity and an excellent adherence to cellophane, glassine paper, and aluminum foil.

One part by weight of natural rubber (pale crepe No. 1), which had been masticated to a Mooney viscosity of 46 $ML_{+1}$ and 1 part by weight of the glycerol ester obtained above were dissolved in toluene to prepare a solution of a concentration of 30% by weight. The resulting solution was coated on cellophane film and dried at 50° C. under reduced pressure for 30 minutes to form an adhesive layer, 40μ in thickness, on the film. The resulting pressure-sensitive adhesive tape showed an excellent tack and adherence.

EXAMPLE 10

Traffic paint test.

A mixture of 100 g of the carboxylic acid of the formula (B') obtained in Example 1, 2.2 g of tall oil fatty acid, 7.1 g of phthalic anhydride, 8.4 g of isophtahlic acid, 7.3 g of glycerol, 16.6 g of pentaerythritol, and 0.6 g of an antioxidant was melted together at 150° C. The molten mixture was further heated, while removing the liberated water, to 260° C. in 3 hours, at which temperature the melt was maintained for a further 4 hours to obtain a modified polyester having a softening point of 94° C. and an acid number of 11.

To 20 parts by weight of the above modified polyester, which had been melted at 180° to 200° C., were added 20 parts by weight of titanium oxide, 15 parts by weight of calcium carbonate, 25 parts by weight of silica sand, 15 parts by weight of glass beads, and 5 parts by weight of an epoxidized soybean oil. The mixture was uniformly mixed to obtain a white traffic paint of the melt application type. This paint was excellent in adherence to road surface, whiteness, weather resistance, and abrasion resistance.

EXAMPLE 11

Into an autoclave were charged 48 g of the fraction of the formula (A) obtained in Example 1, 2.5 g of cobalt acetate tetrahydrate, 7 g of distilled water, and 60 ml of pyridine. After the air in the autoclave had been replaced by hydrogen, carbon monoxide was introduced thereinto until a pressure of 90 kg/cm². The autoclave was heated to 200° C. and maintained at this temperature for 6.5 hours to allow the reaction to proceed. After the completion of the reaction, the catalyst was decomposed with hydrochloric acid and the reaction mixture was washed with water. The oily layer was distilled to obtain 51 g of a fraction boiling at 210°-230° C./3 mmHg.

The above fraction showed a single peak in its liquid chromatogram and had an acid number of 195. The IR spectrum of this product was identical with that of the fraction of the formula (B') in FIG. 11. Therefore, it was confirmed that the product was a mixture of position isomers of the following structural formula (B'):

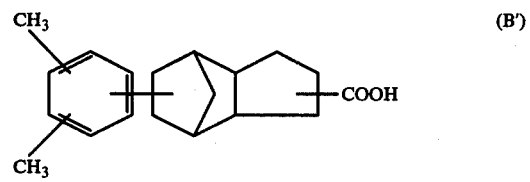

(B')

EXAMPLE 12

In a 50-ml, three-necked flask equipped with a stirrer and a water trap, after the air therein had been sufficiently replaced by nitrogen, were placed 10.2 of the carboxylic acid obtained in Example 1, 1.5 g of pentaerythritol and 5 ml of xylene, and they were melted at 170° C., and further heated to 250° C. for 3 hours in a nitrogen stream while removing the water liberated. After the completion of the reaction, the xylene was distilled off, and the flask was maintained at 250° C. under a reduced pressure of 1 mmHg for 1 hour to distil off the remaining xylene and unreacted materials.

The resulting resin was a pale yellow solid having a softening point of 86.5° C., an acid value of 9 and a hydroxyl value of 37. The elementary analysis values thereof were C 79.8%; H 8.3%; and O 12.1%. In the NMR spectrum thereof, the methylene proton

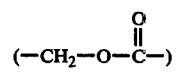

of the ester was observed at 4.04 ppm. Furthermore, in the IR absorption spectrum of the product, the absorption due to the alcohol was observed at 1,030 cm$^{-1}$ and 3,510 cm$^{-1}$, and the absorption due to the ester was observed at 1,170 cm$^{-1}$ and 1,730 cm$^{-1}$. From the above facts, it was confirmed that compounds having the following formula were produced:

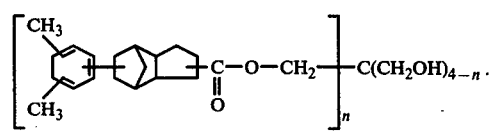

From the above acid value, hydroxyl value, elementary analysis and NMR spectrum, it was confirmed that the product was a mixture of the compounds represented by the above formula wherein n is 1 to 4, and the average value of n was 3.4.

Conditions for measuring NMR spectrum:
Solvent: — Carbon tetrachloride
Concentration: — 20%
Reference: — TMS
Temperature: — 24° C.
Conditions for measuring IR spectrum:
KBr plate coated.

The mixture was fractionated by a liquid chromatography and it was confirmed from the elementary analysis, NMR spectrum and hydroxyl value of each fraction that the compound of n being 1, the compound of n being 2, the compound of n being 3 and the compound of n being 4 were each obtained.

What is claimed is:

1. A cyclopentadiene derivative comparable in performance characteristics to natural rosin, having the general formula:

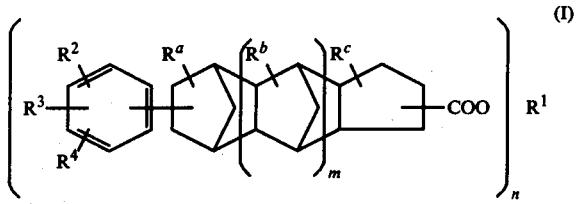

wherein $R^1$ is hydrogen, a mono- to tetra-hydric alcohol moiety having 1 to 12 carbon atoms, a metal of Groups Ia, and IIa of the Periodic Table, an ammonium group or an organic amine residue; $R^2$, $R^3$, and $R^4$ are independently hydrogen or alkyl groups having 1 to 6 carbon atoms; $R^a$, $R^b$, and $R^c$ are independently hydrogen or alkyl groups having 1 to 3 carbon atoms; m is 0 or 1; and n is an integer of 1 to 4.

2. A cyclopentadine derivative according to claim 1, wherein $R^a$, $R^b$ and $R^c$ are hydrogen.

3. A cyclopentadiene derivative according to claim 1, wherein $R^1$ is hydrogen, a mono- to tetra-hydric alcohol moiety having 1 to 6 carbon atoms, sodium, potassium, calcium, magnesium, or ammonium.

4. A cyclopentadiene derivative according to claim 1, wherein $R^1$ is hydrogen, and n is 1.

5. A cyclopentadiene derivative according to claim 1, wherein $R^1$ is Na or K, and n is 1.

6. A cyclopentadiene derivative according to claim 1, wherein $R^1$ is Ca, or Mg, and n is 2.

7. A cyclopentadiene derivative according to claim 1, wherein $R^1$ is a mono- to tetra-hydric alcohol moiety having 1 to 6 carbon atoms.

8. A cyclopentadiene derivative according to claim 1, wherein $R^1$ is ammonium or an organic amine residue, and n is 1.

9. A cyclopentadiene derivative according to claim 1, wherein $R^2$ and $R^3$ are hydrogen, or an alkyl group having 1 to 6 carbon atoms, and $R^4$ is hydrogen.

10. A cyclopentadiene derivative according to claim 1, wherein $R^2$ is hydrogen or an alkyl group having 1 to 6 carbon atoms, and $R^3$ and $R^4$ are hydrogen.

11. A cyclopentadiene derivative according to claim 1, wherein $R^2$, $R^3$, and $R^4$ are independently hydrogen, methyl, ethyl, or isopropyl.

12. A cyclopentadiene derivative according to claim 1, wherein m is 0.

13. The cyclopentadiene derivative of claim 1, wherein $R^1$ is hydrogen, a metal of Groups Ia and IIa of the Periodic Table, or an ammonium group.

14. A cyclopentadiene derivative having the general formula:

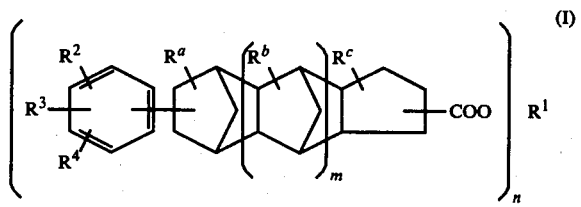

wherein $R^1$ is a metal of Group IIb of the Periodic Table; $R^2$, $R^3$, and $R^4$ are independently hydrogen or alkyl groups having 1 to 6 carbon atoms; $R^a$, $R^b$, and $R^c$ are independently hydrogen or alkyl groups having 1 to 3 carbon atoms; m is 0 or 1; and n is an integer of 1 to 4.

* * * * *